United States Patent [19]

Tribble et al.

[11] 4,308,293
[45] Dec. 29, 1981

[54] ANTIMICROBIAL TREATMENT AND PRESERVATION OF ANIMAL FEEDSTUFFS

[75] Inventors: Talmadge B. Tribble, 1740 E. Mission Hills Rd., Northbrook, Ill. 60062; Gordon W. Rose, Grosse Point Park, Mich.

[73] Assignee: Talmadge B. Tribble, Northbrook, Ill.

[21] Appl. No.: 118,484

[22] Filed: Feb. 4, 1980

[51] Int. Cl.³ .......................... A23K 3/03; A23L 3/34
[52] U.S. Cl. .................................... 426/532; 426/335; 426/636; 426/654; 426/807; 426/271; 424/195; 424/317; 424/319
[58] Field of Search ............... 426/335, 532, 654, 271, 426/807, 636; 424/195

[56] References Cited

U.S. PATENT DOCUMENTS

| | | | |
|---|---|---|---|
| 2,910,367 | 10/1959 | Melnick | 426/532 |
| 3,624,222 | 11/1971 | Nelson | 426/532 |
| 3,903,267 | 9/1975 | Miler et al. | 426/532 |
| 4,083,999 | 4/1978 | Drury | 426/532 |

OTHER PUBLICATIONS

Hackh's Chemical Dictionary, p. 559 "Pyroligneous Acid" McGraw-Hill, N.Y. 1974.
The Merck Index, Merck & Co., Rahway, N.J. 1960, p. 881.

Primary Examiner—Jeanette M. Hunter
Attorney, Agent, or Firm—McCaleb, Lucas & Brugman

[57] ABSTRACT

Pyroligneous acid and pyroligneous acid complexes incorporating selective additives are employed as antifungal, antibacterial preservative agents for the treatment of animal feedstuffs.

14 Claims, No Drawings

ANTIMICROBIAL TREATMENT AND PRESERVATION OF ANIMAL FEEDSTUFFS

This invention relates generally to antifungal and antibacterial treatment and preservation of animal feed and feedstuffs such as high-moisture grains, hay and forage nutrients and to improvements in antimicrobial agents useful in such treatment.

The infection and contamination of animal feedstuffs by molds, fungi, and excessive bacteria generally reduces the nutritional value thereof by impairing the animal's ability to convert and assimilate the nutrients, by depressing the animal's appetite and by creating potential toxicity for the livestock and possible contamination of food products produced from the animal.

The seriousness of the infected feed problem, of the nature outlined above, depends by-in-large on the type of molds and fungus present, the quantity or density of the infecting population and the age and species of the animal being fed. While undoubtedly thousands of bushels of infected grain are fed without any apparent loss in terms of animal performance, more recent studies have given strong indication that infection of feedstuffs may represent more than a minor factor in the depressed performance of feeding livestock. Evidence is also present, aside from potential toxicity to the livestock, that the end products produced by the animal from contaminated feed has a real potential for toxifying the human consumer as well.

For example, *Gibberella zeae* is a mold found on corn and certain other field grains and while it is a naturally occurring fungus, it is particularly serious during wet, cold growing seasons and harvesting periods. Its presence in feed is known to cause animals to refuse to eat, to induce vomiting and to produce an estrogenic effect related to possible abortion and infertility, particularly in swine. It also generates T-2 toxins which are dangerous to both man and animals. Aflatoxin, a metabolic product of the fungus *Aspergillus flavus* also may be present on a wide variety of foods and feeds and under certain conditions will produce mycotoxins which are particularly harmful to mammals, fish and birds. The fungi that produce aflatoxins are widespread and its control is of great economic significance since its generalized effects on farm animals include growth inhibition, decreased feeding effeciency and increased internal organ weight.

While the foregoing examples serve to indicate the seriousness of the microbial problem in animal feeds, suffice it to say that no totally satisfactory solution has heretofore been presented, although the current invention is considered and believed to be a major step in that direction.

The underlying basis of this invention lies in the unexpected finding that pyroligneous acid exhibits antifungal, antibacterial and antimicrobial preservative properties which may be potentiated, modified and buffered by complexing the same with selected additives to effectuate enhanced antimicrobial activity. As a result of our discoveries, an effective, efficient and economic antimicrobial agent, capable of suppressing and attacking bacteria, fungus, molds and similar contaminating microbial populations is available.

In brief, the present invention teaches the antimicrobial protection of animal feedstuffs through the utilization of pyroligneous acid and/or pyroligneous acid complexed with buffering and modifying additives which provide chelating, sequestering, water softening, and surface tension reducing effects and which promote the ability of the pyroligneous acid to effectively penetrate across cell/spore membranes so that the resulting agent is significantly enhanced in its antimicrobial activity. In particular, preferred additives according to this invention comprise ethylenediaminetetra-acetic acid (EDTA) its sodium and/or calcium salts and related compounds plus non-ionic synthetic detergents, such as glycol ethers, for enhancing the antimicrobial effectiveness of pyroligneous acid.

It is an important object of this invention to provide an improved antimicrobial agent for animal feedstuffs incorporating organic compounds of natural origin embodying organic acids, aldehydes and phenolics.

Another important object of this invention is to provide improved antimicrobial agents incorporating ingredients as set forth in the preceding objective, which are safely and effectively potentiated, buffered and modified or controlled in reactivity rate by complexing the same with selected non-toxic additives.

Still another object of this invention is to provide an improved economical and effective antimicrobial agent and preservative for animal feedstuffs employing a blend of naturally occurring non-toxic organic compounds and ingredients demonstrating improved preservative effectiveness.

Having described our invention the above and further objects, features, and advantages thereof will appear from the following description of preferred and modified embodiments, illustrative of its teachings and representing the best mode presently contemplated to enable those of skill in the art to practice this invention.

By way of background to the specifics of our discovery, it is known that certain weakly dissociated organic acids such as formic, acetic, propionic, butyric, valeric, benzoic and sorbic, by way of examples, demonstrate antimicrobial activity thought to be largely dependent upon the undissociated molecules, as well as the anions; the undissociated molecules acting to enhance the antimicrobial activity of the hydrogen ions or to provide independent antimicrobial activity. Further it is recognized that the antimicrobial activity of monobasic organic acids e.g. acetic, propionic, butyric, etc., increases with increase in molecular weight as opposed to dibasic organic acids, such as oxalic, malonic, succinic, etc. McCalla has suggested that the inhibitory effects of hydrogen ions are related to their high adsorbability which prevents the adsorption of essential nutritive ions of low adsorbability by the microbial (bacterial/fungal) cells. [*ANTIMICROBIAL AGENTS*. Llyod W. Hedgecock. Lea and Febiger, Phila. Pa., 1967 PP 78-80] Thus essential nutritive ions of low adsorbability may be displaced from their adsorption sites by the more active hydrogen ions, leading to deficiency of the essential ions required for microbial growth. Further, it is thought that increased intracellular concentrations of the hydrogen ions may alter the structural integrity and solubility of proteins and interfere with the functions of metallic prosthetic groups of enzymes and/or may also produce lethal damage to the surface components of the bacterial cell through hydrolytic reactions.

It is also recognized that amino acids and proteins behave as both weak acids and weak bases since they contain at least one carboxyl and one amino group. Substances which ionize as both acids and bases in aqueous solution are referred to as amphoteric, exemplified by the amino acid glycine, in which both the acidic and basic groups are ionized in solution to form dipolar ions or zwitterions:

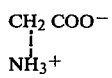

The glycine molecule is electrically neutral since it contains an equal number of positive and negative ions and its zwitterion form therefore would be isoelectric; the pH at which the zwitterion does not migrate in an electric field being referred to as its isoelectric point. Such isoelectric point pH's differ for each protein (e.g. 4.7 for serum albumin, 5.6 for fibrinogen etc.). Amphoteric compounds, e.g. microbial cytoplasmic amino acids and proteins, react with either acids or bases to form salts thusly:

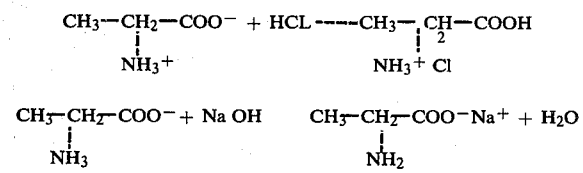

From the above it will be recognized that with the addition of H+ to an isoelectric molecule an increased positive ($NH_3+$) results, since the acid represses the ionization of the carboxyl group. Thus, microbial proteins may be said to change from zwitterion form to a form dissociating as a charged amino group upon coming into contact with either acids or bases which operate to change the isoelectric point pH. The result may be a reduced ionization, solubility and availability of the proteins. [*Essentials of Organic and Biochemistry.* Donald J. Burton and Joseph I. Routh. W. B. Saunders Company, Phila. Pa., 1974 PP 166–182; *Introduction To Physiological and Pathological Chemistry.* L. Earle Arnow and Marie C. Logan. The CV Mosby Company, St. Louis Missouri, 6th Edition, 1961, PP 145–167].

In light of the above, the present invention is directed to the proposition that an effective antimicrobial preservative would be one which provides an acid climate or atmosphere (4–6 pH) in which protein is less soluble and therefore less available to attack by microbial populations.

DESCRIPTION OF PREFERRED EMBODIMENT

Pyroligneous acid, also known as liquid smoke or wood vinegar, is a carbonization condensate of natural smoke in an aqueous vehicle or diluent. The source of the carbonization vapor (smoke) is found in the combustion or carbonization of cellulosic fiber materials, principally hard wood fibers, such as hickory, maple and other hard woods. The resulting solution, known as pyroligneous acid has a concentration which is easily quantifiable and dilution-controlled having a chemical composition which, while not entirely definable, consists generally of the following naturally occurring, organic compounds:

1. Acetic acid, an organic, monobasic, monocarboxylic acid in order of 5.0 to 12.0%.
2. Carbonyl compounds, e.g. aldehydes, ketones, esters, and carboxylic acids; butanone-2 and heptaldehyde as smoke carbonyls.
3. Phenolics (smoke phenols) such as dimethoxyphenol.
4. Propionic acid in small amounts.

The specific gravity of pyroligneous acid is similar to water (1.024 to 1.030 at 25° C.); the unbuffered pH is in the order of 2.0 to 3.0 and the acid is soluble and miscible in water and alcohol. In-use pH values of 4–6 are readily achieved depending on the substrate moisture. Its principal use heretofore has been in the smoking of meats.

In our examination of pyroligneous acid as an antimicrobial agent, the broad spectrum of its properties, with and without enhancing additives, were evaluated against heat-resistant, spore-forming, aerobic bacilli, gram-negative bacillus associated with avian and human enteritis, and various saprophytic molds (mycelial fungi) associated with animal feeds, spoilage and, in several instances, human and animal mycotoxicoses.

In each instance our findings indicate that this substance, effectively and irreversibly reduces natural and/or experimental microbial contaminants associated with animal feedstuffs.

In order to determine the general effectiveness of the antimicrobial activity of pyroligneous acid comparative evaluations thereof with organic acids commonly used as antimicrobial agents, namely, propionic acid and acetic acid were conducted with the following results:

EXAMPLE 1:

PYROLYGNEOUS ACID versus PROPIONIC ACID

A mixed inoculum of *Salmonella typhimurium,* ATCC 14028 and a corn-associated strain of *Aspergillus flavus* was spray-applied to four different polysaccharide/cellulosic substrates at a density of 50,000 organisms/spores per gram of substrate. Pyroligneous acid was applied at a use-rate of 8 ounces per ton of test substrate:

| TEST SUBSTRATES: TREATED, UNTREATED (TEST SAMPLES- 100 GRAMS/SUBSTRATE) | MICROBIAL (BACTERIAL AND MOLD SPORE) DENSITY/GRAM FOLLOWING ONE-WEEK OF INCUBATION AT 26–28° C. | | | |
|---|---|---|---|---|
| | S. typhimurium | | A. flavus | |
| | Pyroligneous Acid | Propionia Acid | Pyroligneous Acid | Propironic Acid |
| 1. CORN MEAL: | 1,000 | 5,000 | 15,000 | 22,000 |
| UNTREATED CONTROL | | (40,000) | | (50,000) |
| 2. WHEAT FLOUR: | 6,000 | 8,000 | 20,000 | 25,000 |
| UNTREATED CONTROL | | (45,000) | | (50,000) |
| 3. RICE HULLS: | 12,000 | 18,000 | 22,000 | 30,000 |
| UNTREATED CONTROL | | (50,000) | | (50,000) |
| 4. SOY GRITS: | 10,000 | 15,000 | 20,000 | 25,000 |
| UNTREATED CONTROL | | (50,000) | | (50,000) |

In accordance with our above findings, it appears that when equal concentrations and volumes of pyroligneous and propionic acids are spray applied to experimentally contaminated cellulosic substrates, pyroligneous acid is 20-30% more effective in reducing the densities of the experimental inocula.

EXAMPLE 2:

Pyroligneous Acid versus Acetic Acid

Sensivity test panel method of evaluation: one-inch panels of Whatman No. 1 chromatography paper (0.16 mm in thickness, medium flow rate) were immersion-soaked in 100% concentrations of the test acids and placed on sensivity agar plate surfaces (Meuller-Hinton with 5% sheep blood) previously "seeded" with test organisms.

| TEST ORGANISMS USED ON "SEEDED" AGAR PLATES | ZONE OF ANTIMICROBIAL ACTIVITY OBSERVED (mm) | |
| --- | --- | --- |
| | Pyroligneous Acid | Acetic Acid |
| Bacillus stearothermophilus, ATCC 7953 | 15.0 | 12.0 |
| Salmonella typhimurium, ATCC 14028 | 10.0 | 9.0 |
| Candida albicans, ATCC 10231 | 14.0 | 13.0 |
| *Aspergillus flavus, ATCC 9643 | 10.00 | 9.0 |
| *Aspergillus niger, ATCC 9642 | 9.0 | 9.0 |
| *Chaetomium globosum, ATCC 6205 | 12.0 | 11.0 |
| *Penicillium funiculosum, ATCC 11797 | 13.0 | 13.0 |

*Meet Military specifications for fungal resistance testing.

From the results obtained under Example 2 above, it is apparent that pyroligneous acid equals or surpasses acetic acid in its ability to control or inhibit antimicrobial activity when evaluated on a sensitivity plate method as indicated.

While the foregoing two examples, demonstrative of the effectiveness of pryoligneous acid as an antimicrobial agent are significant as compared to the corresponding activity of propionic and acetic acid, both recognized and used as antimicrobial agents for the preservation of animal feedstuffs, we have further discovered that such observed beneficial activity of the pyroligneous acid may be enhanced materially by complexing the same with certain chemical additives.

For example, it has been found that safe and effective potentiation of the antimicrobial properties of pyroligneous acid and its effective buffering and modification of its activity rate may be brought about by complexing the same with non-toxic ethylene diamine tetra acetic acid (EDTA), its sodium salt (disodium edetate, Na$_2$ EDTA and/or trisodium salt, Na$_3$ EDTA and/or tetra-sodium salt, Na$_4$ EDTA and/or its calcium salt, Ca EDTA) as well as a number of closely related compounds, which form poorly or slowly dissociable chelate complexes with many divalent and trivalent cations. This same chemical additive also acts as a sequestering agent, a water softener, a penetrant and a surface tension reducing agent.

In addition to the beneficial enhancement effects provided by the additive EDTA as above outlined, we have further discovered that the ability of pyroligneous acid to effectively penetrate across cell/spore membranes is enhanced by incorporating therewith low foaming, non-ionic synthetic detergents (syndets) such as gylcol ethers, which act to uniformly spread the preservative compound over the treated substrate.

The following laboratory data demonstrates the foregoing observations and conclusions:

Using a test inoculum of mixed cultures of *Pseudomanas Sp., Proteus Sp.,* and *Enterobacter Sp.* in equal densities, to a total of $1 \times 10^6$ per gram, pyroligneous acid concentrations with and without enhancing additives were spray applied to experimentally contaminated whole kernel corn. The following preferred formulation of the pyroligneous acid with additives, constituting a base composition for our antimicrobial complex, was employed.

FORMULA I 1. 4.0 grams of a dry sodium and/or calcium salt of EDTA, dissolved in 100 grams of isopropanol (isopropyl alcohol);
2. 4.0 grams of non-ionic synthetic detergent e.g. glycol ether; (Syndet); and
3. sufficient pyroligneous acid to bring the total volume to five gallons (approximately 18,900 grams).

| Pyroligneous acid concentrations (ppm) with and without enhancing additives - spray-applied to experimentally contaminated whole kernel corn | Bacterial density/ gram of mixed test culture inoculum after one week of exposure | Percent (%) reduction of initial density of inoculum ($1 \times 10^6$/gram) |
| --- | --- | --- |
| 500 ppm with 100 ppm tetra-sodium salt of EDTA and 100 ppm of non-ionic syndet additives | 25,000 | 97.5 |
| 500 ppm without additives | 200,000 | 80.0 |
| 400 ppm with additives | 50,000 | 95.0 |
| 400 ppm without additives | 150,000 | 85.0 |
| 300 ppm with additives | 100,000 | 90.0 |
| 300 ppm without additives | 200,000 | 80.0 |
| 200 ppm with additives | 300,000 | 70.0 |
| 200 ppm without additives | 600,000 | 40.0 |

From the foregoing it is observed that by complexing pyroligneous acid with the specified additives of a non-ionic synthetic detergent and the tetra sodium salt of EDTA increases the antimicrobial activity of the pyroligneous acid by approximately 20% or more.

We have further observed that the incorporation of low concentrations of organic acids, such as propionic acid, produces additional enhancement of the antimicrobial activity of pyroligneous acid, substantially in accordance with the following formulation.

FORMULA II 1. 4.0 grams of a dry sodium and/or calcium salt of EDTA, dissolved in 100 grams of isopropanol (isopropyl alcohol);
2. 4.0 grams of a non-ionic synthetic detergent e.g. glycol ether, (Syndet);
3. 8 ounces (approximately 224 grams) of a candidate organic acid, such as propionic acid; and
4. Sufficient pyroligneous acid to bring the total volume to approximately five gallons (approximately 18,900 grams).

The above two formulae/complexes may be applied in practice to various animal nutrients at in-use concentrations ranging from 16 to 80 ounces per ton, the concentration varying with the moisture content of the substrate to be treated. Additionally, water soluble forms of EDTA may be substituted for the listed alcohol soluble forms indicated.

In order to verify the foregoing observations, the following three complexed formulations of pyroligneous acid were evaluated:
1. Pyroligneous Acid plus Trisodium Salt of N-Hydroxyethylene- (diamine triacetic acid)*
2. Pyroligneous Acid Plus diamine triacetic acid plus nonionic synthetic detergent (glycol ether)*
3. Pyroligneous Acid plus diamine triacetic acid plus nonionic synthetic detergent glycol ether plus propionic acid*

*The concentrations of the indicated ingredients/additives were per Formula I and/or II.

METHODOLOGY

The antimicrobial SENSITIVITY TEST PANEL (DISC) METHOD was employed, utilizing one-inch square panels of Whatman No. 1 chromatography paper 0.16 mm in single thickness, medium flow rate. A triple thickness of the "panel" paper was immersion-soaked in each of the candidate formulations, centered on the surface of 100 mm agar plates (Meuller-Hinton with 5.0% sheep blood) previously swab-seeded with test organisms and the activity zone determined.

the pyroligneous acid complex with propionic acid in accordance with formula II, appears to increase the antimicrobial activity of the pyroligneous acid complex of Formula 1 an average of substantially 23% against the test organisms involved.

From the foregoing description of our invention and its modifications, those of skill in the art will readily recognize that pyroligneous acid is a unique antimicrobial preservative compound providing a natural prescription of ingredients, each of which has proven antimicrobial effectiveness. Of no little significance, is the fact that this agent, with or without enhancing additives, per our invention, is a non-corrosive, non-toxic, non-caustic chemical complex which is safer to handle than the more commonly used antimicrobial acetic and propionic acids. While these latter acids are used in high concentrations (50–100%) at given rates of application (i.e. 10 to 20 pounds per ton) in and on animal feed ingredients, such as high moisture corn, pyroligneous acid is, in effect, a non-caustic, less concentrated and therefore safer chemical for animal feed preservation. Further it has been demonstrated that selective additives, as herein taught, effectively enhance the normal antimicrobial activity of this agent in surprising proportions. Be that as it may, pyroligneous acid, per our invention, with or without additives effectively reduces and combats natural or experimentally imposed microbial contaminants associated with animal feed ingredients in satisfaction of our main objective.

RESULTS:

| TEST ORGANISMS USED TO INOCULATE (SEED) THE TEST PLATE SURFACE | ZONE OF ANTIMICROBIAL ACTIVITY OBSERVED (mm) FOLLOWING 72-HOURS INCUBATION AT 37° C. (BACTERIA) AND 96-HOURS INCUBATION AT 28° C. (FUNGI) | | |
|---|---|---|---|
| | 1. Pyroligneous A. + EDTA | 2. Pyroligneous A. + EDTA + Syndet | 3. Pyroligneous A. + EDTA + Syndet + propionic acid |
| *Aspergillus flavus* ATCC 9643 | 13.0 | 15.0 | 21.0 |
| *Aspergillus niger*, ATCC 9642 | 12.0 | 14.0 | 22.0 |
| *Candida albicans*, ATCC 10231 | 7.0 | 10.0 | 16.0 |
| *Chaetomium globosum*, ATCC 6205 | 16.0 | 18.0 | 21.0 |
| *Gibberella zeae*, ATCC 24688 | 15.0 | 17.0 | 19.0 |
| *Trichoderma viride*, QM 9123 | 13.0 | 14.0 | 22.0 |
| *Bacillus cereus*, aerobic spore-former | 12.0 | 15.0 | 22.0 |
| *Bacillus stearothermophilus*, aerobic spore-former, ATCC 7953 | 16.0 | 18.0 | 21.0 |
| *Enterobacter aerogenes*, lactosefermenter, gram-negative | 15.0 | 16.0 | 18.0 |
| *Serratia marcescens*, lysine and ornithine decarboxylase positive | 10.0 | 15.0 | 22.0 |
| *Salmonella typhimurium*, ATCC 14028 | 17.0 | 18.0 | 20.0 |

Our above findings established that the addition of the synthetic detergent, glycol ether, appears to increase the zone of antimicrobial activity by an average of 16% ascribed principally to the increase in penetration and migration of active ingredients as a result of lower surface tension. In addition, the reinforcement of The embodiments of the invention in which an exclusive property or privilege is claimed are defined as follows:

1. An antimicrobial complex for preserving animal feed and feedstuffs selected from the group of grains, hay and forage nutrients, comprising pyroligneous acid, and an enhancer for buffering the activity rate of said acid, selected from the group of ethylene diamine tetra acetic acid (EDTA), the sodium salt thereof, the disodium salt thereof, the trisodium salt thereof, the tetrasodium salt thereof and/or the calcium salt thereof.

2. The complex of claim 1 and a non-ionic, synthetic detergent for enhancing penetration of the complex across cell/spore membranes of a treated substrate.

3. The complex of claim 2 wherein said synthetic detergent is a glycol ether in an amount effective to enhance said penetration across cell/spore membranes.

4. The complex of claim 2, and further including propionic acid in an amount effective to reduce the microbe environmental Ph.

5. An antimicrobial complex for preserving animal feed and feedstuffs selected from the group consisting of grains, hay and forage nutrients, comprising pyroligneous acid, complexed with EDTA and a non-ionic synthetic detergent substantially according to the following proportions:
   4 grams of EDTA;
   4 grams of glycol ether; and
   sufficient pyroligneous acid to bring the total volume to five gallons.

6. The antimicrobial complex of claim 5, and including propionic acid substantially according to the following proportions:
   4 grams of EDTA;
   4 grams of glycol ether;
   224 grams of propionic acid; and
   18,900 grams of pyroligneous acid.

7. An antimicrobial complex for preserving animal feed and feedstuffs selected from the group consisting of grains, hay and forage nutrients, comprising: pyroligneous acid and diamine triacetic or tetra acetic acids in an amount effective for buffering the activity rate of said pyroligneous acid.

8. The complex of claim 7 and a glycol ether non-ionic, synthetic detergent for enhancing penetration of the complex across the cell/spore membranes of a treated substrate.

9. The complex of claim 7 and including propionic acid in an amount effective to reduce the microbe environmental Ph.

10. The complex of claim 9 wherein the recited ingredients are formulated substantially in the proportions of:
    4 grams of said diamine triacetic or tetra acetic acids;
    4 grams of said glycol ether;
    224 grams of said propionic acid; and
    18,900 grams of said pyroligneous acid.

11. Animal feedstuffs selected from the group consisting of grains, hay and forage nutrients, preserved with an antimicrobial complex comprising essentially pyroligneous acid buffered with EDTA, applied to the feed and feedstuffs in concentrations of 16 to 80 ounces per ton.

12. Animal feedstuffs according to claim 11 further enhanced with a glycol ether in an amount effective to promote penetration of the complex across the cell/spore membranes of the feedstuffs.

13. Animal feedstuffs according to claim 12 wherein said complex is further enhanced with propionic acid in an amount effective to reduce the microbe environmental Ph.

14. Animal feedstuffs, preserved with the enhanced complex of claim 13, wherein the ingredients of said complex are formulated substantially in the proportions of:
    4 grams of EDTA;
    4 grams of glycol ether;
    8 ounces of propionic acid; and
    sufficient pyroligneous acid to bring the total volume to five gallons.

* * * * *

UNITED STATES PATENT AND TRADEMARK OFFICE
CERTIFICATE OF CORRECTION

PATENT NO. : 4,308,293

DATED : December 29, 1981

INVENTOR(S) : Talmadge B. Tribble and Gordon W. Rose

It is certified that error appears in the above—identified patent and that said Letters Patent is hereby corrected as shown below:

Column 3, line 25 "3" should be -- 3+ --.

Column 4, in the table, in the second heading under S. typhimurium, "Propionia" should be -- Propionic --.

Signed and Sealed this

Ninth Day of March 1982

[SEAL]

Attest:

GERALD J. MOSSINGHOFF

Attesting Officer

Commissioner of Patents and Trademarks